United States Patent [19]

Weijand et al.

[11] Patent Number: 5,824,029

[45] Date of Patent: Oct. 20, 1998

[54] IMPLANTABLE MEDICAL SYSTEM FOR PERFORMING TRANSTHORACIC IMPEDANCE MEASUREMENTS ASSOCIATED WITH CARDIAC FUNCTION

[75] Inventors: Koen J. Weijand, Hoenbroek, Netherlands; John D. Wahlstrand, Shoreview, Minn.

[73] Assignee: Medtronic, Inc., Minneapolis, Minn.

[21] Appl. No.: 233,901

[22] Filed: Apr. 28, 1994

[51] Int. Cl.⁶ .................................................. A61N 1/05
[52] U.S. Cl. ........................................ 607/122; 600/547
[58] Field of Search ............................ 607/122, 24, 119; 128/734, 713; 600/374, 547, 506

[56] References Cited

U.S. PATENT DOCUMENTS

| | | |
|---|---|---|
| 3,348,548 | 10/1967 | Chardack . |
| 3,915,174 | 10/1975 | Preston . |
| 4,289,134 | 9/1981 | Bernstein . |
| 4,291,699 | 9/1981 | Geddes et al. . |
| 4,407,296 | 10/1983 | Anderson . |
| 4,499,907 | 2/1985 | Kallok et al. . |
| 4,535,774 | 8/1985 | Olson . |
| 4,572,206 | 2/1986 | Geddes et al. . |
| 4,585,004 | 4/1986 | Brownlee ............................ 128/903 |
| 4,686,987 | 8/1987 | Salo et al. . |
| 4,702,253 | 10/1987 | Nappholz . |
| 4,721,110 | 1/1988 | Lampadius . |
| 4,733,667 | 3/1988 | Olive et al. . |
| 4,884,576 | 12/1989 | Alt . |
| 4,962,767 | 10/1990 | Brownlee . |
| 5,003,976 | 4/1991 | Alt . |
| 5,312,440 | 5/1994 | Hirschberg et al. ..................... 607/5 |
| 5,324,327 | 6/1994 | Cohen ................................. 607/122 |
| 5,325,870 | 7/1994 | Kroll et al. ........................... 607/122 |
| 5,336,253 | 8/1994 | Gordon et al. ......................... 607/122 |

OTHER PUBLICATIONS

Principles of Exercise Responsive Pacemakers, Neale E. Fearnot, Ph.D., Leslie A. Geddes, M.E., Ph. D., F.A.C.C. and Heidi J. Smith, Purdue University, IEEE Engineering in Medicine and Biology Magazine, Jun. 1984, pp. 25–29.

Vagal Stimulation After Myocardial Infarction: Accentuating the Positive*, James E. Sneddon, Yaver Bashir, MRCP, David E. Ward, MD. FACC, London, England, United Kingdom, MRCP, 1993 by the American College of Cardiology, Nov. 1, 1993:1335–7, pp. 1335–1337.

Inter–Office Memorandum, To: Koen J. Weijand, From: Joseph F. Breimayer, Subject: Impedance Sensing Lead, Dated 06 Sep. 1988.

Miniature Electrodes Do Double Duty in Implantable Automatic Defibrillator, Technology News, EDN, Aug. 5, 1978, p. 40.

Orthoganal Electrogram Sensing, PACE, vol. 6, p. 464, 1983.

Alternative Modes for Physiological Pacing, T.D. Bennett, W. H. Olson, G. A. Bornzin, M.D. Baudino, in: Francisco Perex Gomes, et al. Cardiac Pacing: Electrophysiology. Tachyarrhythmia. Futura Publishing Company. Mount Kisco, NY 1985. pp. 577–587.

Primary Examiner—William E. Kamm
Assistant Examiner—Kennedy J. Schaetzle
Attorney, Agent, or Firm—Michael J. Jaro; Harold Patton

[57] ABSTRACT

A method and apparatus for deriving impedance signals with an implanted pulse generator and lead system. In particular the present invention provides a medical system which delivers electrical stimulation pulses to a first area and senses impedance in a second area, in particular the medical system features a multi electrode lead connectable to a pulse generator through a standardized connector assembly. The lead has two internal conductors and three electrodes. Two of the electrodes are coupled by means of a capacitor integral with the lead.

39 Claims, 8 Drawing Sheets

F I G. I

IMPLANTABLE MEDICAL SYSTEM FOR PERFORMING TRANSTHORACIC IMPEDANCE MEASUREMENTS ASSOCIATED WITH CARDIAC FUNCTION

FIELD OF THE INVENTION

This invention relates generally to a medical system which delivers electrical stimulation pulses to a first area and senses impedance in a second area, in particular the medical system features a multi electrode lead connectable to a pulse generator through a standardized connector assembly.

BACKGROUND OF THE INVENTION

A wide variety of cardiac pacing systems are known and commercially available. A cardiac pacing system generally comprises a pulse generator and at least one lead. Pacing systems are often characterized according to the lead configuration used. Two of the more popular lead configurations are called "unipolar" and "bipolar."

In general, a unipolar lead has a single electrode disposed at the distal end of the insulative lead body. The single electrode is electrically connected to the pulse generator by a conductive wire which extends through the lead body.

A bipolar lead, in contrast, typically has two electrodes. A "tip" electrode is disposed at the distal end of the insulative lead body. A "ring" electrode is disposed proximally back from the distal end of the lead. Each electrode is electrically connected to the pulse generator by a conductive wire. Each conductive wire is typically insulated and extends through the lead body.

Located at the proximal end of the typical pacing lead is a connector assembly. Connector assemblies typically are provided according to the pacing industry standard. IS-1 UNI designates the industry standard connector assembly for a unipolar lead. IS-1 BI designates the industry standard connector assembly for a bipolar lead.

Standardized connector assemblies provide several advantages. First, because the same connector assembly may be used for different leads, a manufacturer can devote fewer of its resources to providing a greater variety of leads. Standardization also gives the physician greater flexibility in prescribing a particular implantable device. This flexibility is particularly advantageous in situations involving substitution of a new and/or improved pulse generator for an existing one. In such situations, replacement of the existing leads may be unnecessary if the existing pulse generator and its replacement fit a common, standardized connector assembly.

One type of popular pulse generator used is what is referred to as a "rate-responsive" pulse generator. A rate-responsive pulse generator varies the pacing rate according to an output from an activity sensor. Typically the pacing rate is variable between a programmable maximum and minimum level. When the output from the activity sensor indicates the patient's activity level has increased, the pacing rate is increased from the programmed lower rate. The amount in which the pacing rate is increased is determined as a function of the output of the activity sensor. That is, the rate-responsive or "target" pacing rate in a rate-responsive pulse generator is determined as follows:

$$TR = PLR + f(\text{sensor output})$$

where TR is a target rate, PLR is a programmed lower rate and f(sensor output) is typically a linear or monotonic function of the sensor output. As long as patient activity continues to be indicated, the pacing rate is periodically increased by incremental amounts calculated according to the above formula, until the programmed upper rate limit is reached. When patient activity ceases, the pacing rate is gradually reduced, until the programmed lower rate limit is reached.

For any rate-responsive pulse generator, it is desirable for the sensor output to correlate as closely as possible with the actual metabolic and physiologic needs of the patient, so the resulting rate-responsive pacing rate may be adjusted to appropriate levels.

Minute ventilation ($V_c$) is one parameter which correlates closely to the actual metabolic and physiologic needs of the patient. "Minute ventilation" as used herein is defined by the equation:

$$V_c = RR \times VT$$

where RR=respiration rate in breaths per minute (bpm), and VT=tidal volume in liters. Clinically, the measurement of $V_c$ can be performed by having the patient breathe directly into a device that measures the exchange of air and computes the total volume per minute. The direct measurement of $V_c$ is not practical with an implanted device. $V_c$ can be indirectly measured, however, by monitoring impedance changes in the patient's thoracic cavity. Such impedance measurements can be performed with implantable circuitry and implantable leads as is known in the prior art.

In general, the measurement of the impedance between two or more sensing locations is referred to as rheography. A pulse generator with rheographic capabilities can measure thoracic impedance in a patient by delivering a known current between two of the pulse generator's electrodes. A pulse generator capable of measuring thoracic impedance with rheography is disclosed in U.S. Pat. No. 4,702,253 to Nappholz and hereby incorporated by reference herein in its entirety. In the Nappholz arrangement, the magnitude of the change of the impedance signal corresponds to the tidal volume and the frequency of change corresponds to respiration rate.

U.S. Pat. No. 4,721,110 issued to Lampadius discloses an arrangement which sets the base pacing rate, in part, according to a rheographically-obtained respiration rate signal. Because rheographic current pulses can interfere with the sensing of electrical cardiac signals, the Lampadius arrangement delivers rheographic current pulses only during the refractory period immediately preceding delivery of a stimulating pulse.

There are currently several commercially-available devices which employ rheographic techniques to adjust the pacing rate according to metabolic needs. For example, the Biorate device manufactured by Biotec International, Bologna, Italy, uses a bipolar, e.g. two-electrode configuration, rheographic arrangement to monitor the patient's respiratory rate. The Meta-MV device manufactured by Telectronics, Pacing Systems, Inc., Englewood, Colo. uses a tripolar rheographic arrangement to monitor the patient's respiratory rate. The Precept device manufactured by CPI, St. Paul, Minn., uses a tetrapolar rheographic arrangement to monitor the patient's pre-ejection interval (PEI), stroke volume (SV), and heart tissue contractility.

Other parties have explored the use of rheographic techniques to monitor physiological parameters. U.S. Pat. No. 4,291,699 to Geddes et al., for example, discloses an impedance-based method and apparatus for detecting cardiac fibrillation. Impedance between a tip electrode and a distal ring electrode is measured. A lack of change in impedance over a period of time is taken as an indication of fibrillation.

One problem with the system disclosed by Geddes is noise. Specifically due, in part, in the Geddes system one of the impedance sensing electrode is positioned proximate to the ventricular apex. At this position the electrode undergoes a relatively large amount of motion, specifically bumping or contacting the myocardial tissue. Such motion and particularly such contact gives rise to electrical noise. In addition polarization effects caused by the pacing pulses through the electrode may also provide noise. Such noise is sensed during impedance measurement, leading to possibly erroneous measurements or requiring complex filtering circuits or both.

Correlation of breathing and intrathoracic pressure fluctuations with impedance of blood in the heart is also recognized in U.S. Pat. No. 4,884,576 to Alt, which describes the measurement of impedance between two electrodes. Low-pass filtering of the impedance signal yields a signal from which the patient's respiratory rate can be derived. High-pass filtering of the same signal yields a signal from which the patient's cardiac activity can be derived.

Many of the prior art impedance-measuring arrangements involve the use of non-standard leads having three, four, or more separate electrodes and insulated conductors. Such leads are disclosed, for example, in U.S. Pat. No. 4,733,667 to Olive et al. (four conductors and four electrodes); U.S. Pat. No. 4,686,987 to Salo et al. (three conductors and three electrodes); and U.S. Pat. No. 4,289,134 to Bernstein (three conductors and three electrodes). Provision of three or more electrodes and conductors may facilitate the use of lead to perform multiple functions (e.g., impedance sensing, electrocardiogram sensing, and cardiac stimulation) and may minimize the possibility that performance of one function may interfere with the performance of another. It would be desirable, however, to provide an impedance-sensing apparatus which could accommodate a conventional lead, e.g., a two conductor, two electrode industry-standard bipolar pacing/sensing lead.

It would be further desirable to provide such a conventional lead to deliver stimulation pulses in a first area and sense impedance in a second area to thereby minimize noise.

Moreover, it is believed there is room for improvement in the circuitry for deriving impedance-based signals, so that various parameters, such as respiration, stroke volume, cardiac systole, and the like, can be accurately detected and differentiated without the need for overly complex circuitry.

SUMMARY OF THE INVENTION

The present invention is directed to a method and apparatus for obtaining impedance-based signals representative of such physiological parameters as cardiac systole, respiration, and stroke volume. In particular, the present invention concerns a medical system which delivers electrical stimulation pulses to a first area and senses impedance in a second area, in particular the medical system features a multi electrode lead connectable to a pulse generator through a standardized connector assembly.

In accordance with one aspect of the present invention, a medical system having a pulse generator and bipolar lead is provided in which the bipolar lead feature a industry standard connector assembly. The lead has three electrodes, a first electrode at the lead tip, a second electrode spaced proximally from the lead tip and a third electrode spaced proximally from the second electrode. The third electrode is coupled to the tip electrode by a capacitor. The capacitor is integrally formed into the lead.

In accordance with another aspect of the present invention, impedance sensing circuitry within an implantable pulse generator causes the delivery of excitation pulses between the first and second electrodes on the lead. Because the excitation pulses are delivered at a frequency at which the capacitor provides a conductive path for the excitation between the first and third electrodes, as well as the relative sizes of the electrodes, substantially all the excitation signals are conducted between the third electrode and the second electrode. In such a manner the intracardiac impedance between the second and the third electrode may be ascertained. From this signal both cardiac function and respiration may be derived. In addition, stimulation or pacing pulses are not conducted to the third electrode by the capacitor, as such stimulation signals are delivered between first electrode and second electrode.

In accordance with another embodiment, the capacitor may also be coupled between the second electrode and an indifferent electrode outside the heart, e.g., the pulse generator's canister. In this embodiment, excitation signals are preferably delivered between the indifferent electrode and the second electrode on the lead. Measurement of the voltage between the indifferent electrode and the first electrode provides a signal representative of transthoracic cardiac impedance. Stimulation or pacing pulses are not conducted to the indifferent electrode by the capacitor, as such stimulation signals are delivered between first electrode and second electrode.

BRIEF DESCRIPTION OF THE DRAWINGS

The present invention may be better appreciated with reference to the following detailed description and the accompanying drawings wherein.

DETAILED DESCRIPTION OF THE INVENTION

The present invention provides a method and apparatus for sensing cardiac function. Specifically a medical system method and apparatus which delivers electrical stimulation pulses to a first area and senses impedance in a second area, in particular the medical system features a multi electrode lead connectable to a pulse generator through a standardized connector assembly.

Figure 1:
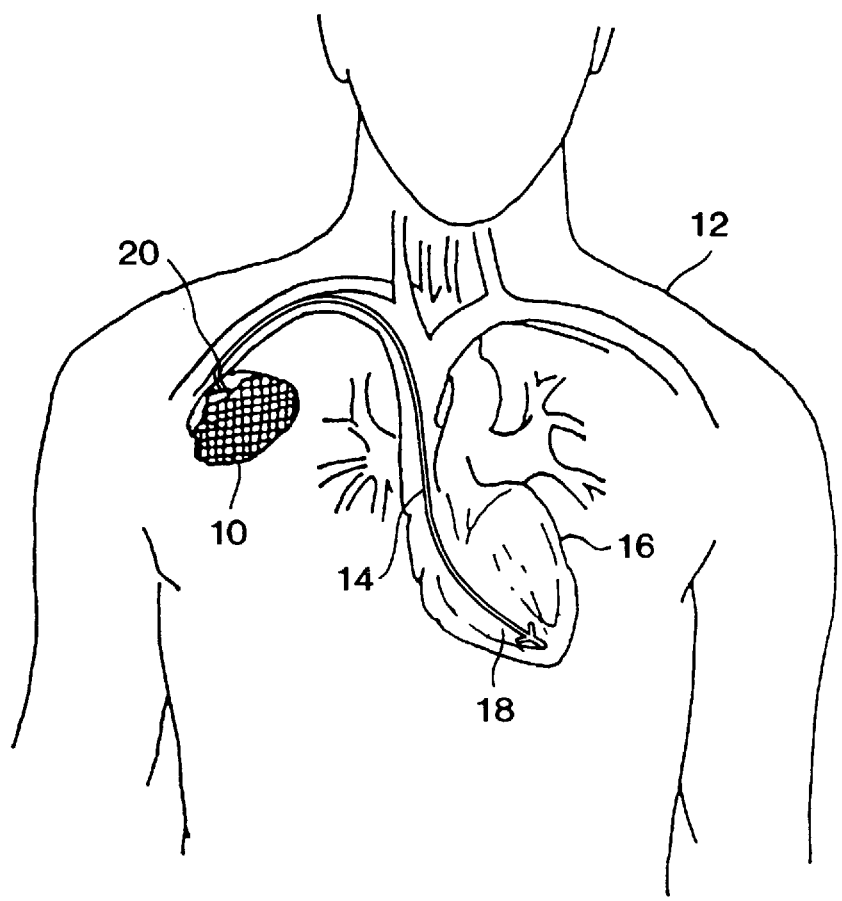
FIG. 1 is an illustration of an implantable pulse generator and lead system in accordance with one embodiment of the present invention, implanted within a patient.

FIG. 1 illustrates the manner in which a cardiac pulse generator 10 and an elongate flexible lead 14 may be implanted in the heart 16 of a patient 12 in accordance with one embodiment of the present invention. Pulse generator 10 may be any of the various known types of pulse generators. It is believed the present invention may be particularly advantageously practiced in conjunction with rate-responsive pulse generators such as the Legend™, Legend Plus™ and Activitrax™ pulse generators available from Medtronic, Inc., Minneapolis, Minn.

Although the present invention shall be described in the context of an implantable pulse generator system, this is only done to illustrate various aspects of the present invention. It is to be understood the present invention may be practiced in conjunction with various types of implantable therapeutic devices, including, for example defibrillators, cardioverters, and the like.

Pulse generator 10 is housed within a hermetic canister. Lead 14 is coupled to pulse generator 10 by means of connector block 20 which receives connector assembly 33 of lead 14, best seen in FIG. 2a.

As shown in FIG. 1, lead 14 extends transvenously from connector 20. Distal end of lead 14 is positioned within right ventricle 18 of heart 16. The position of lead 14 within heart 16 may be more clearly appreciated with reference to FIGS. 2 and 2a.

Figure 2:
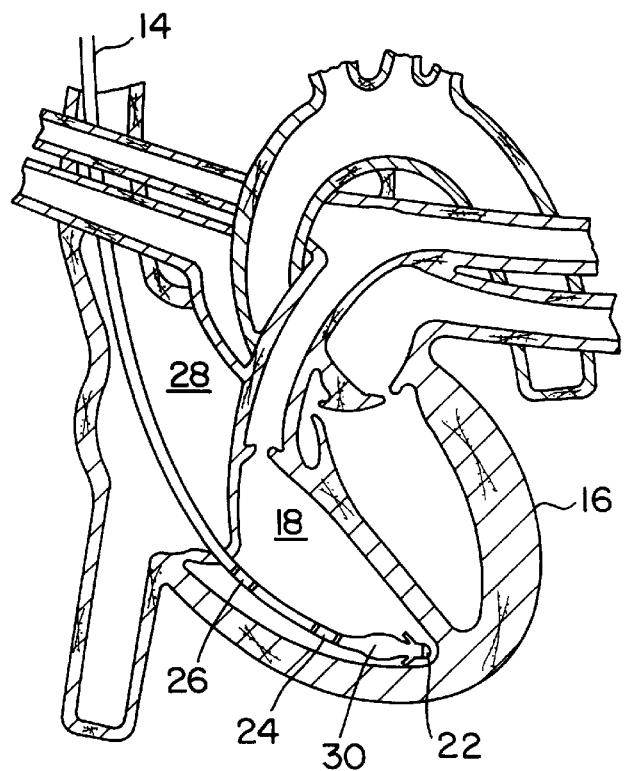
FIG. 2 is an illustration of the distal end of a lead in accordance with one embodiment of the present invention, disposed in a patient's heart.

Referring to FIG. 2, lead 14 is provided with a "tip" electrode 22 at the extreme distal end of lead 14. A "ring" electrode 24 (RING1) is disposed on the body of lead 14 at a point spaced back from the distal end of lead 14, and a second "ring" electrode 26 (RING2) is disposed on the body of lead 14 at a point spaced back from the second electrode 24. In the presently preferred embodiment of the invention, RING1 electrode 24 is spaced back approximately 2-cm from the distal end of lead 14, and RING2 electrode 26 is spaced back approximately 4-cm from the distal end of lead 14. With such spacing, and with distal end of lead 14 positioned generally in the apex of ventricle 18, RING1 electrode 24 is disposed more or less centrally within ventricle 18 while RING2 electrode 26 is disposed generally at the top of ventricle 18. As will be hereinafter described in greater detail, it is contemplated that it may be suitable for the purposes of practicing the present invention that the spacing of RING2 electrode 26 is such that RING2 electrode 26 is actually disposed within the right atrium 28, although positioning RING2 electrode 26 within ventricle 18 is believed to be preferable.

Although RING1 electrode 24 and RING2 electrode 26 are preferably whole ring electrodes, they may also be of other geometries such as split ring or orthoganal electrodes, as seen, in the U.S. Pat. No. 4,962,767 entitled "Pulse generator Catheter" to Brownlee or the article of Goldreyer, et al. "Orthoganal Electrogram Sensing" PACE, V. 6, pg. 464, 1983.

Figure 3:
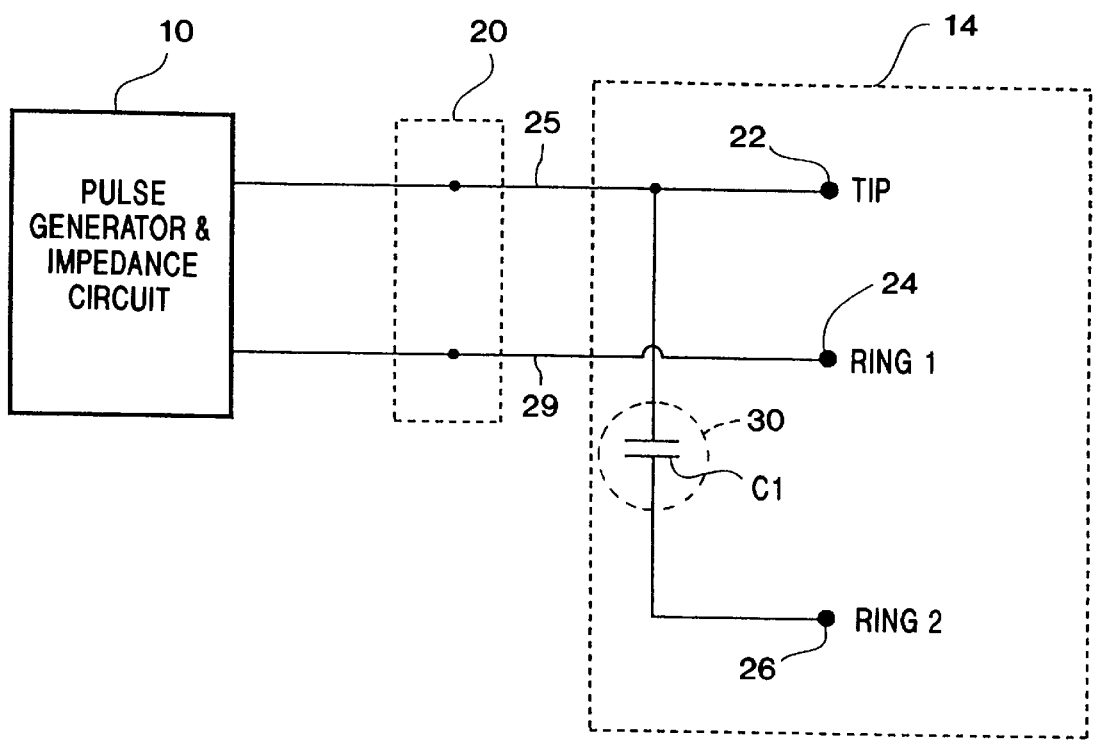
FIG. 3 is an electrical schematic representation of the pulse generator and lead system from FIG. 1 configured for intracardiac impedance sensing.

Although having three electrodes, tip electrode 22, RING1 electrode 24 and RING2 electrode 26, lead 14 has only two separate internal conductors 25, 29. As best depicted in FIG. 3 conductors 25, 29 extend along lead 14 and are connected at their respective proximal ends to pulse generator 10. As previously noted a conventional bipolar connector block 20 is used to provide the connection. In the preferred embodiment conductors 25, 29 comprise a standard arrangement of a coiled wire, preferably a platinum iridium alloy as is well known in the art. Although conductors 25, 29 are provided coaxially, in the alternative they may be provided in a side-by-side configuration, as seen in the U.S. Pat. No. 3,348,548 to Chardack.

Figure 2A:
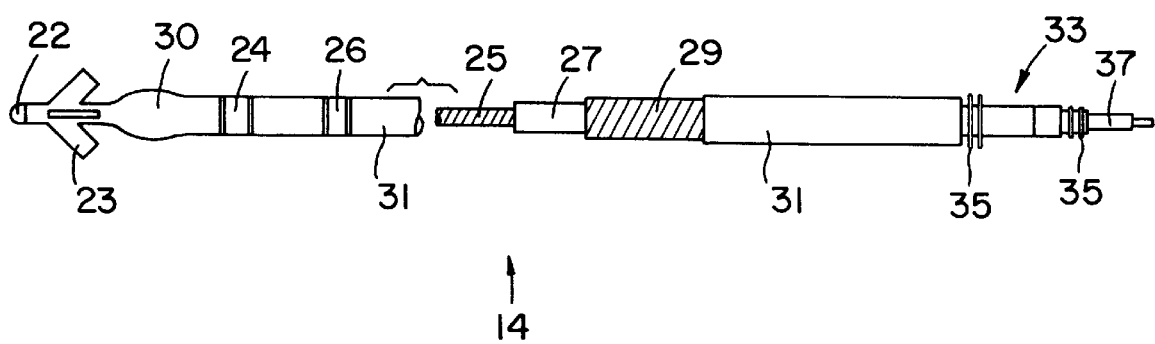
FIG. 2a is a plan view of a lead depicted in FIG. 2.

Lead 14 and specifically conductor 25 is provided with an internal capacitor C1 is positioned within hermetic enclosure 30, as shown in FIGS. 2 and 2a. Capacitor C1 provides an electrical connection between tip electrode 22 and RING2 electrode 26. Hermetic enclosure 30 may be provided along lead 14 according to the teachings of U.S. Pat. No. 4,407,296 to Anderson, entitled "Integral Hermetic Implantable Pressure Transducer" and assigned to the assignee of the present invention and hereby incorporated by reference herein in its entirety. Specifically hermetic enclosure 30 may be provided through provision of a titanium enclosure housing a ceramic mounting. Ceramic mounting is preferably constructed from a glass, as is well known in the art. Mounted within ceramic mounting is capacitor C1. Hermetic enclosure 30 is covered by an insulative material, such as silicone.

In the alternative, hermetic enclosure 30 may be provided by potting the capacitor C1 in an epoxy, such as HYSOL, as is well known in the art. Once potted within the epoxy, capacitor C1 would be integrally formed within the lead 14.

As best seen in FIG. 2a lead 14 has a plurality of tines 23 proximate tip electrode 22 as is well know in the art. Lead 14 has inner conductor 25 covered by inner insulator 27. Over inner insulator 27 is outer conductor 29, covered, in turn, by outer insulator 31. At proximal end of lead 14 is connector assembly 33. Connector assembly 33 is of a standardized design, IS-2 BI as illustrated, and thus may readily connect to a corresponding standard connector block 20 of a pulse generator 10, as depicted in FIG. 2. Connector assembly 33 features sealing rings 35 and connector pin 37 and is constructed in a fashion well know in the art. Inner insulator 27 and outer insulator 31 are preferably of a biocompatible material, such as silicone or polyurethane.

Figure 4:
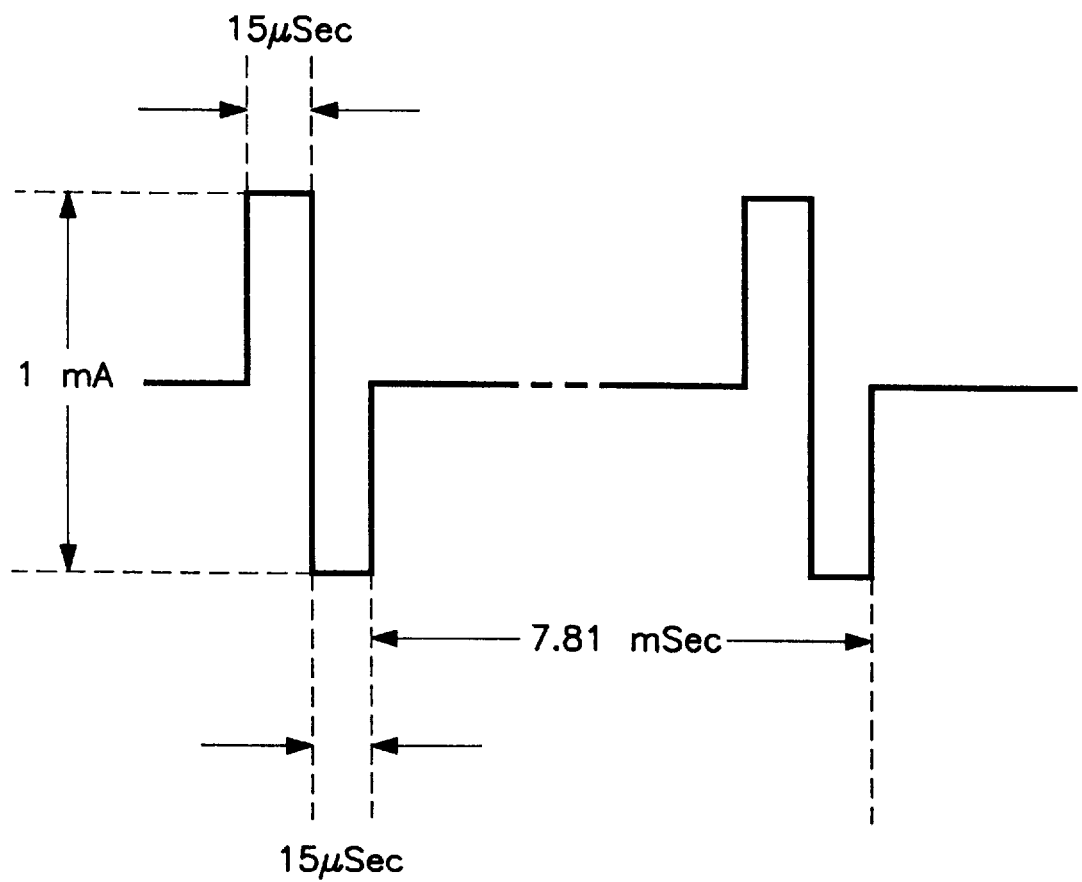
FIG. 4 is a diagram of a biphasic excitation signal used in the present invention.

FIG. 3 shows a diagrammatic representation of pulse generator 10 (including impedance circuitry, to be hereinafter described in greater detail) and lead 14 with electrodes 22, 24 and 26, and capacitor C1. Conventional bipolar connector block 20 is also shown schematically in FIG. 3, coupling the two conductors of lead 14 to pulse generator 10. As shown in FIG. 3, capacitor C1, contained within hermetic enclosure 30 of lead 14, couples tip electrode 22 to RING2 electrode 26. Surface area of RING2 tip electrode 26 is relatively larger than the surface area of tip electrode 22. Thus, as is explained in further detail below, due to the relative dimensions of the electrodes along with the relatively small capacitor C1 along with the use of a high frequency impedance measuring signal (as depicted in FIG. 4), the present invention permits the sensing of impedance between RING1 electrode 24 and RING2 electrode 26, while permitting pacing pulses to be delivered via tip electrode 22 to RING1 electrode 24. In short the present invention provides a medical system and lead which may deliver electrical stimulation pulses to a first area and sense intracardiac impedance in a second area, such lead connectable to a pulse generator by means of a conventional bipolar connector block.

In the preferred embodiment tip electrode 22 has a surface area of 12 sq. mm and is a porous platinized platinum alloy. RING1 electrode 24 has a surface area of 48 sq. mm and RING2 electrode 26 has a surface area of 48 sq. mm and each are preferably constructed from a polished platinum alloy, although other constructions, such as a porous platinized platinum alloy or a ridged electrode surface may also be used. Capacitor C1 preferably has capacitance value in the range of approximately 10- to 100-nF.

Impedance measurement can be accomplished by driving a known current between implanted electrodes and then measuring the resultant voltage changes. From such voltage changes impedance can be determined according to Ohm's law. See, for example, the above-referenced Alt '576 patent. As discussed above, from such impedance changes both respiration and cardiac function may be determined. The Medtronic Legend Plus™ pulse generator (currently undergoing clinical trials in the United States) measures impedance through a biphasic stimulus between the pulse generator canister and a ring electrode of a transvenous pacing/sensing lead. The sampled waveform is processed to remove noise (as discussed above) and to determine a signal which is proportional to the respiration rate and tidal volume. From these values minute ventilation may be calculated. The minute ventilation is then used, in part, to set the pacing rate.

Figure 10:
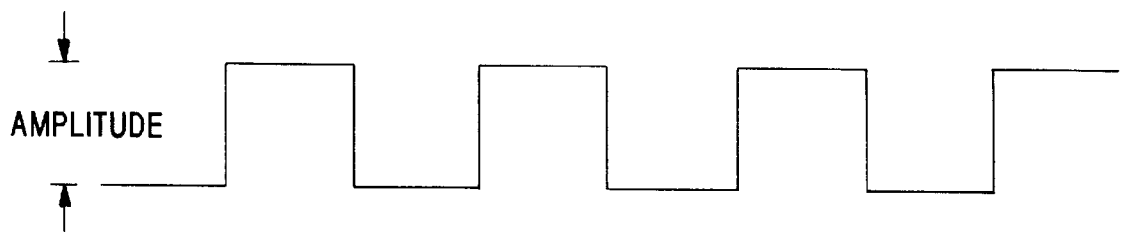
FIG. 10 is a diagram of an alternative excitation signal used in the present invention.

FIG. 4 shows the biphasic current excitation signal utilized in the Legend Plus™, and which is also believed to be suitable for the purposes of practicing the present invention. The current excitation signal comprises a sequence of 1.0-mA (peak-to-peak) pulses of 30-μSec duration (15-μSec positive polarity, 15-μSec negative polarity. Such pulses are delivered at a frequency of 128-Hz, i.e., one pulse every 7.81-mSec, although it is believed the delivery of biphasic pulses at other frequencies, e.g., 16-, 64-, 256-Hz, etc. . . . , may also be acceptable for the purposes of practicing the present invention. Moreover, although the current excitation signal preferably comprises a sequence of 1.0-mA (peak-to-peak), it may additionally have a range, including from between 0.5 mA to 2.0 mA (peak-to-peak). Still further, the present invention may also utilize pulses as shown in FIG. 10, having an amplitude of between 10–100 μA and a frequency of 4 KHz. Other frequencies and waveforms may also be used, if desired.

Excitation current pulses depicted in FIG. 4 are generated by impedance measuring circuitry included within pulse generator 10, as depicted in FIG. 3. In particular, the high frequency biphasic excitation pulses are delivered at a frequency on the order of 128-Hz or so, as noted above. Because capacitor C1 is relatively small, approximately 10- to 100-nF as discussed above, and is coupled to tip electrode 22 which has a relatively small surface area as compared to RING2 electrode 26, 12 sq. mm versus 48 sq. mm respectively, also discussed above, the high frequency biphasic excitation pulses substantially conduct or flow between RING2 electrode 26 and RING1 electrode 24.

In contrast, although capacitor C1 provides a conductive path for biphasic pulses between RING1 electrode 24 and RING2 electrode 26, pacing pulses (which are delivered at a lower frequency), are not similarly affected by the presence of capacitor C1. Thus while the substantial portion of the high frequency biphasic pulses are conducted between RING1 electrode 24 and RING2 electrode 26, the relatively lower frequency pacing pulses are substantially conducted between tip electrode 22 and RING1 electrode 24. In short, electrical stimulation pulses are delivered to a first area and impedance is sensed in a second area.

It has been the inventors' experimental experience that the presence of capacitor C1 has no adverse impact upon effective pacing and also tends to significantly improve the resolution and clarity of resulting impedance signals detected between RING1 electrode 24 and RING2 electrode 26, as compared with such signals in prior art impedance sensing configurations.

Figure 5A:
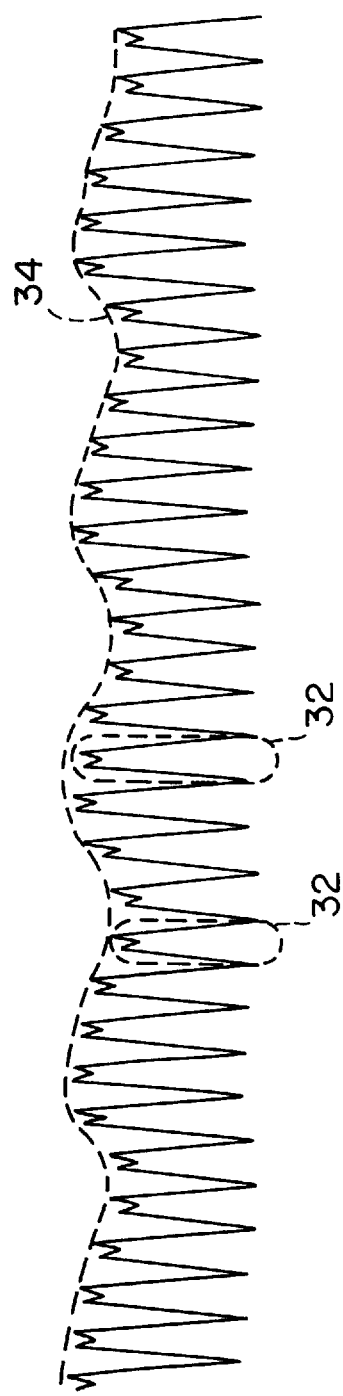
FIGS. 5a and 5b diagram intracardiac impedance signals obtained from the lead of FIGS. 1 and 2.

Referring to FIG. 5a, for example, a reading between RING1 electrode 24 and RING2 electrode 26 is shown for a capacitor value of C1 of 10-nF and in which biphasic pulses are delivered between RING1 electrode 24 and RING2 electrode 26 at a rate of 128-Hz. As seen both cardiac systole and respiration can be observed in the signal shown in FIG. 5a. In particular, each oscillation of the signal (such as the individual ones identified with reference numerals 32 in FIG. 5a) is representative of a cardiac beat, with the change in impedance reflected by the oscillation resulting from the change in the volume of blood in the heart during a cardiac cycle. In addition, the oscillations in peak values of the signal of FIG. 5a, as represented by the dashed line 34, represent respiration. Through appropriate filtering, a signal representative of cardiac systole only, as well as a signal representative of respiration only, could also be derived from the composite signal of FIG. 5a.

Figure 5B:
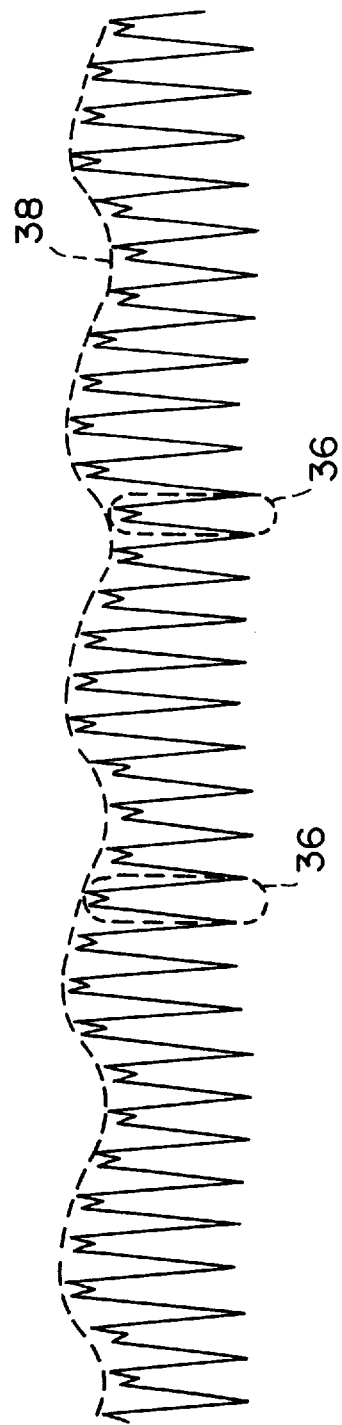

FIG. 5b shows another impedance sensing signal corresponding to a reading of the voltage between RING1 electrode 24 and RING2 electrode 26 taken while a series of biphasic excitation pulses are delivered at a rate of 128-Hz between RING1 electrode 24 and RING2 electrode 26. For the signal depicted in FIG. 5b, capacitor C1 has a value of 56-nF rather than the 10-nF value used in connection with FIG. 5a. As in the signal depicted in FIG. 5a, the signal depicted in FIG. 5b shows both cardiac systole and respiration, with cardiac systole being evidenced by oscillations such as those identified by reference numerals 36, and respiration being evidenced by the oscillatory variations in peak values of oscillations 36, as represented by dashed line 38. It should be understood, however, the waveforms shown in FIGS. 5a and 5b are shown in an AC manner without regard to polarity. The modulation of the signal by respiration could also occur during diastole which corresponds to lower impedance.

Based on experimental data, such as is illustrated in FIGS. 5a and 5b, it is contemplated that a capacitance value in the range of approximately 10 to 100-nF is preferable for the intracardiac impedance sensing arrangement shown in FIG. 3.

Figure 6:
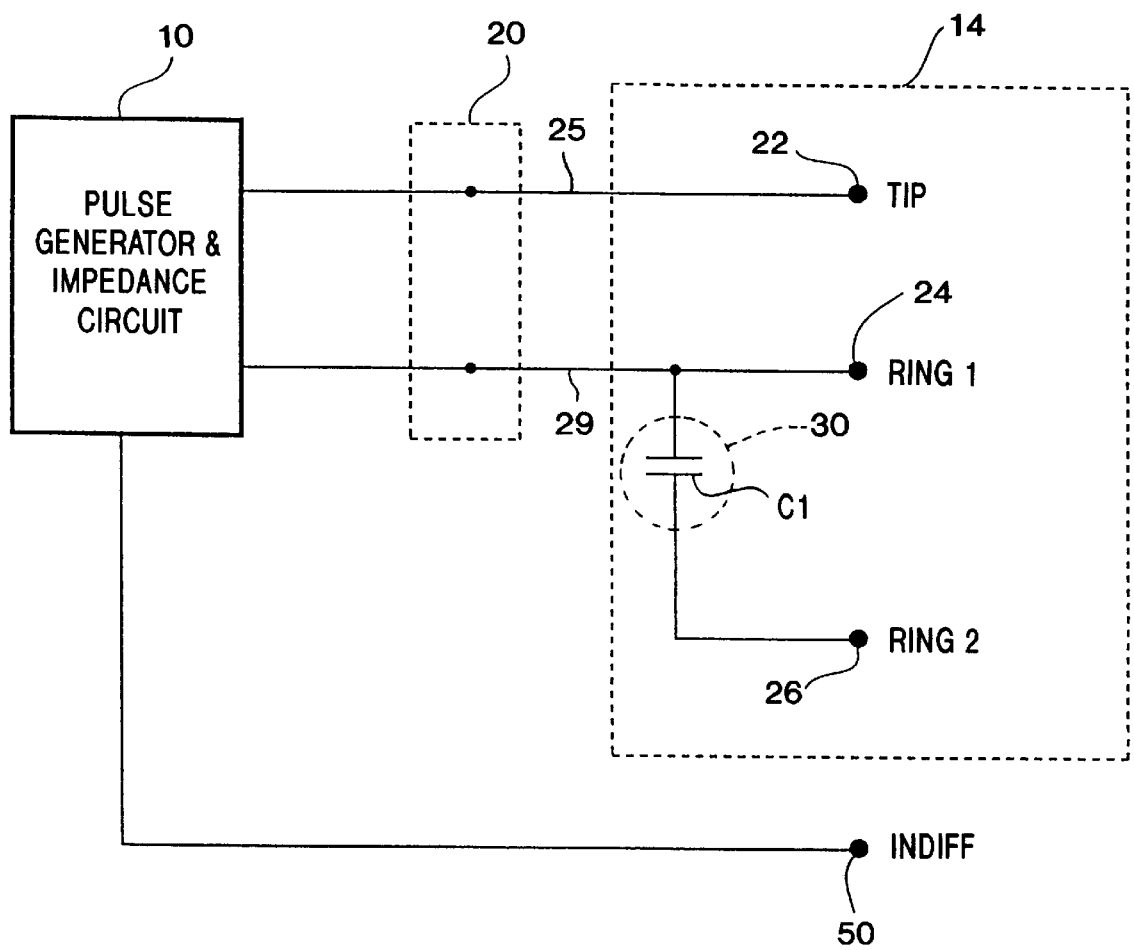
FIG. 6 is an electrical schematic representation of the pulse generator and lead system from FIG. 1 configured for transthoracic impedance sensing.

FIG. 6 shows an alternative embodiment of the present invention configured for performing transthoracic impedance sensing rather than for performing intracardiac impedance sensing as previously described. Those components of the embodiment of FIG. 6 which are identical to components in the embodiment of FIG. 3 have retained identical reference numerals. Capacitor C1 is coupled, however, between RING1 electrode 24 and RING2 electrode 26 rather than between tip electrode 22 and RING2 electrode 26 as in the intracardiac impedance embodiment seen in FIG. 3.

For the embodiment depicted in FIG. 6, excitation pulses from pulse generator 10 are delivered between RING1 electrode 24 and INDIFF electrode 50 at a frequency of 16-Hz to 128-Hz or so. Capacitor C1 establishes a conductive path for the excitation pulses between RING1 electrode 24 and RING2 electrode 26. Further sensing circuitry associated with pulse generator 10 measures the voltage between INDIFF electrode 50 and tip electrode 22, in order to compute transthoracic impedance according to Ohm's law.

Figure 7:
FIG. 7 is a diagram of a transthoracic impedance signal obtained from the lead of FIGS. 1 and 2 in accordance with the principles of the present invention.

An example of the transthoracic impedance signal obtained through the use of a sensing configuration in accordance with the embodiment shown in FIG. 6 is shown in FIG. 7. The signal in FIG. 7 represents the voltage between tip electrode 22 and INDIFF electrode 50 (i.e., the pulse generator canister) when biphasic excitation pulses (see FIG. 4) are delivered between RING1 electrode 24 and INDIFF electrode 50 at a rate of 16-Hz, and when a capacitor C1 has a capacitance value of 100-nF. Those of ordinary skill in the art will appreciate that, as compared with the intracardiac impedance signal previously described with reference to FIGS. 3, 5a, and 5b, cardiac systole is less dominant while the effects of respiration are more dominant in the transthoracic impedance signal in FIG. 7.

Figure 8:
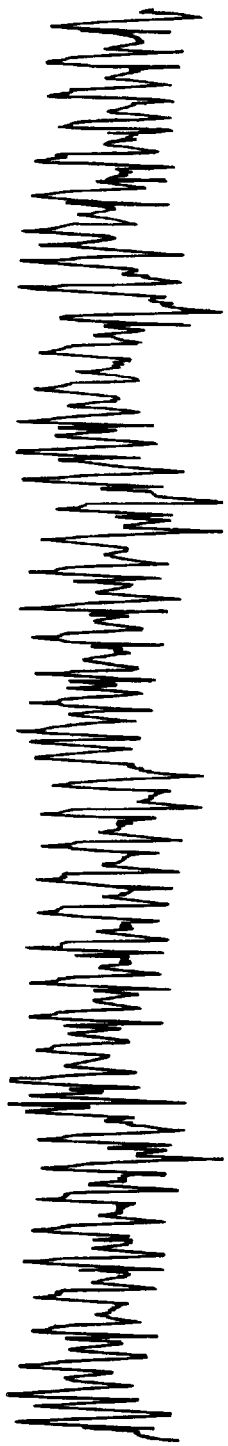
FIG. 8 is a diagram of a prior art intracardiac impedance signal.

A comparison between either FIGS. 5a or 5b and FIG. 8 illustrates the advantage of the present invention. FIG. 8 shows an impedance signal obtained from the delivery of excitation pulses between a pulse generator's canister and the ring electrode of a conventional bipolar lead, and wherein sensing is performed between the tip electrode of the bipolar lead and the pulse generator canister. As seen neither cardiac systole nor respiration are clearly represented in FIG. 8, especially as compared to either FIGS. 5a or 5b. Of course filtering and other signal processing may be used in order to derive useful respiration or cardiac rate signals from the raw impedance signal of FIG. 8. This filtering and/or signal processing may lead to increased size, cost, and complexity.

Figure 9:
FIG. 9 is a diagram of a prior art transthoracic impedance signal.

Similarly, FIG. 9 shows a transthoracic impedance signal obtained using a prior art device having only a conventional bipolar lead. Again, respiration is not as dominant in the signal of FIG. 9 as it is in the transthoracic signal of FIG. 7.

Figure 11:
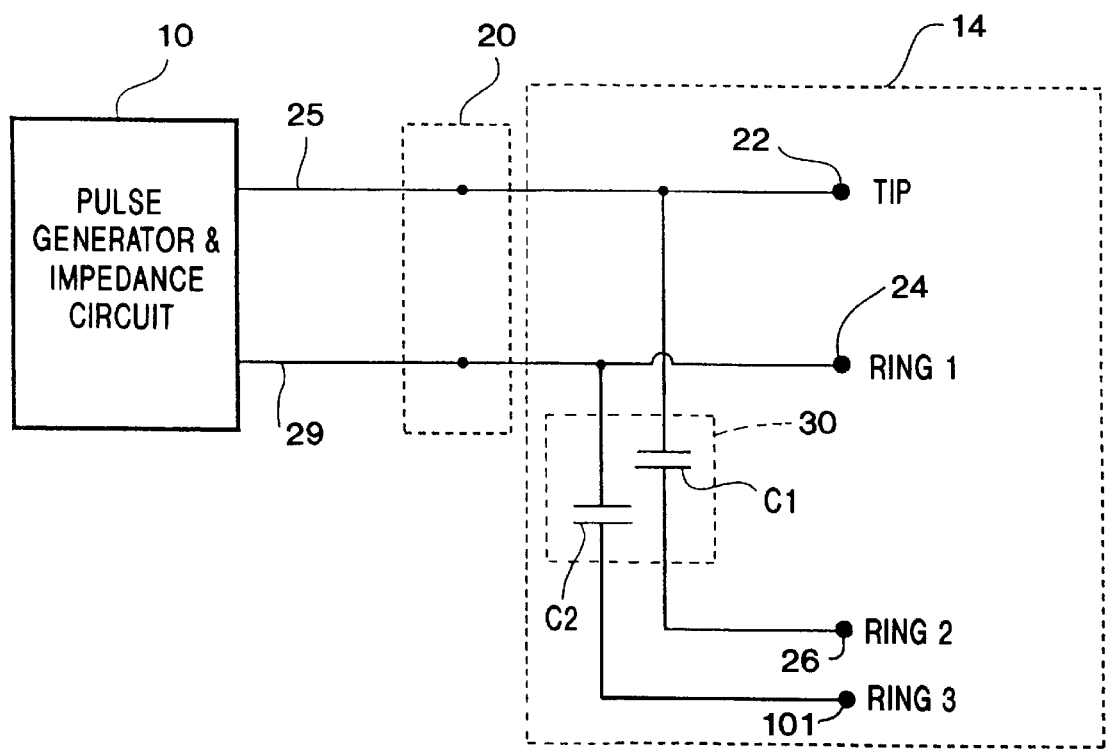
FIG. 11 shows a still further alternative embodiment of the present invention.

FIG. 11 shows a still further alternative embodiment of the present invention. Those components of the embodiment of FIG. 11 which are identical to components in the embodiment of FIG. 3 have retained identical reference numerals. Essentially, this embodiment is a lead featuring a pair of electrodes 22, 24 each of which is capacitively coupled to another electrode. Specifically, electrode 22 is capacitively coupled to electrode 26 by capacitor C1 and electrode 24 is capacitively coupled to electrode 101 by capacitor C2. Through such a configuration, stimulation pulses may be conducted between electrode 22 and electrode 24 while impedance measuring signals may be conducted between electrode 26 and electrode 101. As in the embodiments previously described, the relative surface areas as well as values for the capacitors along with the frequency of an amplitude of the impedance measuring signal must be coordinated together for the lead to operate as intended.

Moreover, while a two pairs of electrodes may be used as seen in the embodiment of FIG. 11, the present invention may also be practiced using a plurality of electrodes capacitively coupled together to thereby permit stimulation in a first plurality of areas and impedance measurement in a second plurality of areas.

Although particular embodiments of the invention have been disclosed, this has been done for illustration only and is not intended to limit the scope of the invention. It is to be understood other expedients known to those skilled in the art or disclosed herein may be employed without departing from the spirit of the invention or the scope of the appended claims, including substituting elements or components which perform substantially the same function in substantially the same way to achieve substantially the same result for those described herein. For example, while particular dimensional values, electronic component values, e.g. capacitor C1, and operational parameter values, e.g. biphasic excitation signal frequency, have been identified, such values may be modified. Moreover, particular components may even be replaced and still be within the scope of the present invention. These replaceable components, for example, may include substituting a filtering system in place of capacitor C1 or capacitor C2 or both.

What is claimed is:

1. A medical electrical lead for performing impedance sensing associated with cardiac function comprising:
   a lead body having a distal end and a proximal end, said lead body having a first conductor and a second conductor each extending along said lead body, said lead body having a terminal assembly disposed upon said proximal end for providing a connection between said plurality of conductors and a connector block of a medical device;
   a first electrode coupled to said first conductor, said first electrode disposed on said lead body;
   a second electrode coupled to said second conductor, said second electrode disposed on said lead body at a point spaced proximally back from said first electrode; and
   a third electrode capacitively coupled to said second electrode, said third electrode disposed on said lead body at a point spaced proximally back from said first electrode.

2. A medical electrical lead in accordance with claim 1 wherein said capacitive coupling is provided by a capacitor coupled between said third electrode and one of said first and second electrodes.

3. A medical electrical lead in accordance with claim 2 wherein said capacitor has a capacitance of between 10-nF and 100-nF.

4. A medical electrical lead in accordance with claim 2 further comprising a canister integrally formed with said lead body for hermetically enclosing said capacitor.

5. A medical electrical lead in accordance with claim 1 wherein said third electrode is capacitively coupled to said first electrode.

6. A medical electrical lead in accordance with claim 1 wherein said second electrode is disposed on said lead body at a point spaced proximally back from said first electrode a distance of 2 cm.

7. A medical electrical lead in accordance with claim 1 wherein second electrode is disposed on said lead body at a point spaced proximally back from said first electrode a distance of 4 cm.

8. A medical electrical lead in accordance with claim 1 wherein said first electrode has a surface area of 12 sq. mm.

9. A medical electrical lead in accordance with claim 1 wherein said second electrode has a surface area of 48 sq. mm.

10. A medical electrical lead in accordance with claim 1 wherein said third electrode has a surface area of 48 sq. mm.

11. A medical device system for performing impedance measurements comprising:
    a pulse generator housed within a canister, said pulse generator having first and second terminals;
    a bipolar connector block disposed on said canister for facilitating connection from outside said canister to said first and second terminals of said pulse generator;
    a lead body having a distal end and a proximal end, said lead body having a first conductor and a second conductor each extending along said lead body, said lead body having a terminal assembly disposed upon said proximal end for providing a connection between said first and second conductors and said connector block of said pulse generator;
    a first electrode coupled to said first conductor, said first electrode disposed on said lead body;
    a second electrode coupled to said second conductor, said second electrode disposed on said lead body at a point spaced proximally back from said first electrode; and a third electrode capacitively coupled to said second electrode.

12. A medical electrical lead in accordance with claim 11 wherein said third electrode is disposed on said pulse generator canister.

13. A medical electrical lead in accordance with claim 11 wherein said third electrode is disposed on said lead body at a point spaced proximally back from said first electrode.

14. A medical electrical lead in accordance with claim 11 wherein said capacitive coupling is provided by a capacitor coupled between said third electrode and one of said first and second electrodes.

15. A medical electrical lead in accordance with claim 14 wherein said capacitor has a capacitance of between 10-nF and 100-nF.

16. A medical electrical lead in accordance with claim 14 further comprising a canister integrally formed with said lead body for hermetically enclosing said capacitor.

17. A medical electrical lead in accordance with claim 11 wherein said third electrode is capacitively coupled to said first electrode.

18. A medical electrical lead in accordance with claim 11 wherein third second electrode is disposed on said lead body at a point spaced proximally back from said first electrode a distance of 2 cm.

19. A medical electrical lead in accordance with claim 11 wherein third second electrode is disposed on said lead body at a point spaced proximally back from said first electrode a distance of 4 cm.

20. A medical electrical lead in accordance with claim 11 wherein said first electrode has a surface area of 12 sq. mm.

21. A medical electrical lead in accordance with claim 11 wherein said second electrode has a surface area of 48 sq. mm.

22. A medical electrical lead in accordance with claim 11 wherein said third electrode has a surface area of 48 sq. mm.

23. An implantable medical device system for performing transthoracic impedance measurements associated with cardiac function, said system comprising:
   an implantable pulse generator housed within a conductive canister, said pulse generator having first and second terminals;
   a bipolar connector block disposed on said canister for facilitating connection from outside said canister to said first and second terminals of said pulse generator;
   an implantable lead having a flexible, elongate lead body with a first and a second conductor extending internally along its length, and having a terminal assembly disposed upon the proximal end thereof for affecting connection between said first and second conductors and the connector block of an implantable medical device;
   a first electrode coupled to said first conductor and disposed at a distal end of said lead body;
   a second electrode coupled to said second conductor and disposed on said lead body at a point spaced proximally back from said first electrode; and
   a third electrode capacitively coupled to said second electrode by a capacitor coupled between said second and third electrodes, said third electrode disposed on said lead body at a point spaced proximally back from said first and second electrodes;
   an excitation circuit associated with said pulse generator and coupled to said first pulse generator terminal and to said conductive canister, said excitation circuit adapted to deliver excitation current pulses between said first pulse generator terminal and said canister;
   a sensing circuit associated with said pulse generator and coupled to said second pulse generator terminal to monitor voltages between said second pulse generator terminal and said canister resulting from delivery of said excitation current pulses.

24. An implantable medical device system in accordance with claim 23 further comprising a canister integrally formed with said lead body for containing said capacitor.

25. A medical electrical lead for performing impedance sensing associated with cardiac function comprising:
   a lead body having distal end and a proximal end, said lead body having a first conductor and a second conductor;
   a first electrode coupled to said first conductor, said first electrode disposed on a distal end of the lead body;
   a second electrode coupled to said second conductor, said second electrode disposed on said lead body at a point spaced proximally back from said first electrode; and
   a third electrode coupled to said first conductor by a capacitor, said third electrode disposed on said lead body at a point spaced proximally back from said second electrode, the capacitor having a capacitance of between 10-nF and 100-nF.

26. A medical electrical lead in accordance with claim 25 further comprising a canister integrally formed with said lead body for hermetically enclosing said capacitor.

27. A medical electrical lead in accordance with claim 25 wherein said second electrode is disposed on said lead body at a point spaced proximally back from said first electrode a distance of 2 cm.

28. A medical electrical lead in accordance with claim 25 wherein third second electrode is disposed on said lead body at a point spaced proximally back from said first electrode a distance of 4 cm.

29. A medical electrical lead in accordance with claim 25 wherein said first electrode has a surface area of 12 sq. mm.

30. A medical electrical lead in accordance with claim 25 wherein said second electrode has a surface area of 48 sq. mm.

31. A medical electrical lead in accordance with claim 25 wherein said third electrode has a surface area of 48 sq. mm.

32. A medical device system for performing cardiac stimulation and impedance measurements comprising:
   means for producing biphasic cardiac pacing pulses at a first frequency;
   means for producing biphasic current excitation signals at a second frequency, the second frequency being higher than the first frequency;
   a medical electrical lead electrically coupled to the means for producing biphasic cardiac pacing pulses and the means for producing biphasic current excitation signals, the medical electrical lead having a first electrode at a distal end, a second electrode proximal to the first electrode and a third electrode proximal to the second electrode, means for delivering the biphasic cardiac pacing pulses between the first electrode and the second electrode to perform cardiac stimulation; means for delivering the biphasic current excitation signals between the first electrode and the third electrode; and
   means for sensing the biphasic current excitation signals delivered between the first electrode and the third electrode.

33. The medical device system according to claim 32 wherein the means for delivering the biphasic cardiac pacing pulses between the first electrode and the second electrode to perform cardiac stimulation comprise a first conductor coupled to the first electrode and a second conductor coupled to the second electrode, and the means for delivering the biphasic current excitation signals between the first electrode and the third electrode comprise a capacitor integrally formed with the medical electrical lead.

34. The medical device system according to claim 32 wherein the capacitor has a capacitance of between 10-nF and 100-nF.

35. The medical device system according to claim 34 wherein said second electrode is disposed on said lead body at a point spaced proximally back from said first electrode a distance of 2 cm.

36. The medical device system according to claim 34 wherein third second electrode is disposed on said lead body at a point spaced proximally back from said first electrode a distance of 4 cm.

37. The medical device system according to claim 32 wherein said first electrode has a surface area of 12 sq. mm.

38. The medical device system according to claim 32 wherein said second electrode has a surface area of 48 sq. mm.

39. The medical device system according to claim 32 wherein said third electrode has a surface area of 48 sq. mm.

* * * * *